(12) United States Patent
Burkhardt et al.

(10) Patent No.: US 7,973,171 B2
(45) Date of Patent: Jul. 5, 2011

(54) PROCESS FOR SYNTHESIS OF DIALKOXYORGANOBORANES

(76) Inventors: Elizabeth Burkhardt, Bridgeville, PA (US); William Atkins, Evans-City, PA (US)

( * ) Notice: Subject to any disclaimer, the term of this patent is extended or adjusted under 35 U.S.C. 154(b) by 0 days.

(21) Appl. No.: 12/947,238

(22) Filed: Nov. 16, 2010

(65) Prior Publication Data

US 2011/0060163 A1  Mar. 10, 2011

Related U.S. Application Data

(62) Division of application No. 11/917,257, filed as application No. PCT/EP2006/063044 on Jun. 9, 2006, now Pat. No. 7,858,827.

(60) Provisional application No. 60/690,113, filed on Jun. 13, 2005.

(51) Int. Cl.
*C07D 207/00* (2006.01)
*C07D 231/00* (2006.01)

(52) U.S. Cl. ......................... 548/405; 548/110

(58) Field of Classification Search .................. 548/110, 548/405

See application file for complete search history.

(56) References Cited

U.S. PATENT DOCUMENTS

| 3,027,396 A | 3/1962 | Willcokson et al. |
| 3,203,928 A | 8/1965 | Willcockson et al. |
| 3,375,265 A | 3/1968 | Fetterly et al. |
| 3,853,941 A | 12/1974 | Hough et al. |
| 5,264,585 A | 11/1993 | Blacklock et al. |
| 5,463,131 A | 10/1995 | Burkhardt |
| 6,037,505 A * | 3/2000 | Quallich ...................... 568/881 |

FOREIGN PATENT DOCUMENTS

WO  WO-02/22623 A1  3/2002

OTHER PUBLICATIONS

Beckman, et al., "Ring Strain in Boroxine Rings: Computational and Experimental Considerations", Journal of Organometallic Chemistry, vol. 633, No. 1-2, pp. 149 to 156, 2001.
Dahlhoff, et al., "Boron Compounds. 45.' 6-Deoxy-O-Acyl-Alpha-L-Mannofuranoses Via O-Ethylboranediyl Derivatives", J. Org. Chem., vol. 42, No. 19, pp. 3151 to 3157, 1977.
Brown, et al. "Organoboranes. 31. A Simple Preparation of Boronic Esters From Organolithium Reagents and Selected Trialkoxyboranes", Organometallics, vol. 2, pp. 1316 to 1319, 1983.
Corey, et al., "Reduction of Carbonyl Compounds With Chiral Oxazaborolidine Catalysts: a New Paradigm for Enantioselective Catalysis and a Powerful New Synthetic Method", Angew. Chem. Int. Ed., vol. 37, pp. 1986 to 2012, 1998.
Miyaura, et al., "Palladium-Catalyzed Cross-Coupling Reactions of Organoboron Compounds", Chem. Rev., vol. 95, pp. 2457 to 2483, 1995.
Brown, Herbert C., at al., "Organoboranes. 30. Convenient Procedures for the Synthesis of Alkyl-And Alkenylboronic Acids and Esters", Organometallics, vol. 2, pp. 1311 to 1316, 1983.
Dahlhoff, et al., "Selective Syntheses of the Methyl a-D-Furanosides of Lyxose and Mannose Using Ethyl(Dimethoxy) Borane", Liebigs Ann. Chem., vol. 8, pp. 807 to 810, 1990.
Corey, et al., "A New Process for the Generation of 1,3,2-Oxazaborolidines, Catalysts for Enantioselective Synthesis", Tetrahedron Letters, vol. 33, No. 29, pp. 4140 to 4144, 1992.
Chavant, et al., "Preparation of Some Organo-Bis (Diisopropylamino) Boranes and Their Application to the Synthesis of Oxazaborolidines", Journal of Organometallic Chemistry, vol. 455, pp. 37 to 46, 1993.

* cited by examiner

*Primary Examiner* — Jafar Parsa
(74) *Attorney, Agent, or Firm* — Connolly Bove Lodge & Hutz LLP

(57) ABSTRACT

The invention relates to a process for the synthesis of dialkoxyorganoboranes, in particular to a process for the synthesis of dialkoxyorganoboranes by an ester exchange reaction. Moreover, the invention relates to a process for the synthesis of organo-oxazaborolidine catalysts (organo-CBS) and of trialkylboroxins. Furthermore, the invention relates to methods of using dialkoxyorganoboranes for the preparation of organo-CBS catalysts and in Suzuki-type coupling reactions.

2 Claims, No Drawings

PROCESS FOR SYNTHESIS OF DIALKOXYORGANOBORANES

RELATED APPLICATIONS

This application is a divisional application of U.S. patent application Ser. No. 11/917,257, filed Dec. 12, 2007, which is a national stage application (under 35 U.S.C. §371) of PCT Application No. PCT/EP2006/063044, filed Jun. 9, 2006, which claims benefit of U.S. Provisional Patent Application No. 60/690,113, filed Jun. 13, 2005.

FIELD OF THE INVENTION

The invention relates to a process for the synthesis of dialkoxyorganoboranes, in particular to a process for the synthesis of dialkoxyorganoboranes by an ester exchange reaction. Moreover, the invention relates to processes for the synthesis of organo-oxazaborolidine catalysts (organo-CBS) and of trialkylboroxins. Furthermore, the invention relates to methods of using dialkoxyorganoboranes for the preparation of organo-CBS catalysts and in Suzuki-type coupling reactions.

BACKGROUND OF THE INVENTION

Dialkoxyorganoboranes are versatile reagents for organic syntheses and have for example been employed in so diverse fields as in the synthesis of antibiotics, insecticides and organoborohydrides. Dialkoxymethylboranes can potentially be used for the synthesis of methyl-substituted chiral oxazaborolidines (known as MeCBS named after Corey, Bakshi and Shibata. c.f. Corey, E. J. et al., Angew. Chem. Int. Ed., 37, 1986-2012 (1998)), which are powerful enantioselective catalysts for ketone reductions. Another potential use for dialkoxyorganoboranes is in Suzuki-type coupling reactions to introduce an organo group into a molecule under formation of a new C—C-bond (Miyaura, N.; Suzuki, A., Chem Rev. 95, 2457-2483 (1995)).

U.S. Pat. No. 5,463,131 describes the preparation of dialkoxyalkylboranes by reacting excess trialkyborates with diborane in the presence of an olefin, e.g.:

$$4B(OR)_3 + B_2H_6 + 6C_2H_4 \cdots \rightarrow 6Et\text{-}B(OR)_2 \text{ (R is alkyl)}$$

Of course, dialkoxymethylboranes cannot be prepared by that method.

Another method for the manufacture of dialkoxyalkylboranes comprises esterification of alkylboronic acids (Brown, H. C. et al., Organometallics 2(10), 1311-1316 (1983), Brown, H. C. et al., Organometallics 2(10), 1316-1319 (1983)) or trialkylboroxins (Dahlhoff, W. V. et al., Liebigs Ann. Chem. 8, 807-810 (1990)) with an appropriate alcohol.

$$R\text{—}B(OH)_2 + 2R'OH \cdots \rightarrow R\text{—}B(OR')_2 + 2H_2O$$

$$(R\text{—}BO)_3 + 6R'OH \cdots \rightarrow 3R\text{—}B(OR')_2 + 3H_2O \text{ (R, R' is alkyl)}$$

Water is generated in these reactions, which very often disturbs further application of the product, even if only traces of water remain.

Water is especially detrimental to the function of the alkyl-CBS catalysts, which can be prepared from dialkoxyalkylboranes. For this reason Corey proposed the use of bis(trifluoroethoxy)alkylboranes for the synthesis of ethyl- and n-butyl-CBS derivatives to avoid the formation of water as a by-product (Corey, E. J. et al., Tetrahedron Lett. 33(29), 4141-4144 (1992)). The use of bis(dialkylamino)alkyloboranes for the synthesis of alkyl-CBS catalysts has also been described (Chavant, P. Y. et al., J. Organomet. Chem. 455, 37-46 (1993)), but these are quite expensive reagents.

It was one object of the present invention to provide a simple and efficient process for the preparation of dialkoxyorganoboranes. The formation of water or other by-products, that might be difficult to handle or to remove, should be avoided during the process. It was another object of the present invention to establish a process for the production of organo-oxazaborolidine catalysts (organo-CBS) using dialkoxyorganoboranes. In addition, a new and efficient method for the preparation of trialkoxyboroxins should be developed.

SUMMARY OF THE INVENTION

Accordingly, the present invention provides a novel process for the preparation of dialkoxyorganoboranes of the formula $R^1\text{—}B(OR^2)_2$, comprising the step of reacting a triorganoboroxin of the formula $(R^1\text{—}BO)_3$ with a trialkylborate of the formula $B(OR^2)_3$ (wherein $R^1$ and $R^2$ are defined hereinafter). Furthermore, improved processes for the manufacture of organo-CBS catalysts using dialkoxyorganoboranes as starting material and of trialkoxyboroxins are disclosed. In addition, new methods of using dialkoxyorganoboranes for the preparation of organo-CBS catalysts and in Suzuki-type coupling reactions are provided.

DETAILED DESCRIPTION OF THE INVENTION

According to the invention the process for the synthesis of the dialkoxyorganoboranes (3) of the formula $R^1\text{—}B(OR^2)_2$ involves an ester exchange reaction between a triorganoboroxin (1) of the formula $(R^1\text{—}BO)_3$ and a trialkylborate (2) of the formula $B(OR^2)_3$, wherein $R^1$ is $C_1$-$C_{20}$ alkyl, $C_3$-$C_{10}$ cycloalkyl, $C_6$-$C_{14}$ aryl, $C_7$-$C_{24}$ aralkyl, $C_7$-$C_{24}$ alkaryl, $C_2$-$C_{20}$ alkenyl, $C_5$-$C_{15}$ cycloalkenyl, $C_2$-$C_{20}$ alkynyl, $CH_2SiMe_3$, substituted $C_1$-$C_{20}$ alkyl
and $R^2$ is $C_1$-$C_{20}$ alkyl, or two $R^2$ groups in compounds 2 or 3 together with the —$BO_2$— moiety form a cyclic structure of the formula

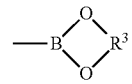

with the divalent group $R^3$ selected from the group consisting of —$CH_2CH_2$—, —$CH(CH_3)CH_2$—, —$CH_2CH_2CH_2$—, —$CH(CH_3)CH(CH_3)$—, —$CH(CH_2CH_3)CH_2$—, $C(CH_3)_2C(CH_3)_2$—, —$CH_2C(CH_3)_2CH_2$—, —$(CH_2)_6$—, ortho-$C_6H_4$ or ortho-$C_6H_3$alkyl With $R^3$ being a divalent group as defined above, the trialkylborates (2) may have the following dinuclear structure:

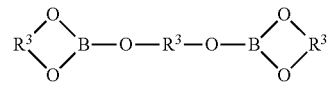

the resulting dialkoxyorganoboranes (3) may have the following cyclic structure:

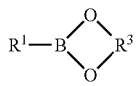

Preferred derivatives prepared by the process according to the present invention are dialkoxyarganoboranes (3) of the formula $R^1$—$B(OR^2)_2$, wherein $R^1$ is methyl, ethyl, n-propyl, isopropyl or n-butyl and $R^2$ is isopropyl or n-butyl.

The reaction is preferably performed under exclusion of air and moisture. The dialkoxyorganoborane (3) is preferably separated from the reaction mixture by distillation. The reaction is preferably carried out in the presence of at least one non-coordinating solvent. Any non-coordinating solvent or mixtures thereof can be employed, preferably with a boiling point different (higher or lower) from that of the dialkoxyorganoborane (3) prepared in order to facilitate its easy separation from the product. For instance, a mixture of two solvents having boiling points below that of compound (3) may be employed. It is also possible to for example use a mixture of two solvents having boiling points higher than that of compound (3) while it may also be advantageous to employ a mixture of solvents having boiling points below and above that of the dialkoxyorganoborane (3) to be prepared. In most cases only one solvent will be employed. Examples are tetrahydrofurane (THF), diethylether, tert.-butylmethylether, hexane, pentane, toluene or benzene, preferably THF or toluene.

The temperature range for the synthesis is from −20° C. and +120° C., preferably from 0° C. and 60° C., more preferably at about ambient temperatures such as from 20 to 30° C. The synthesis is usually performed at a pressure from 0.1 bar to 5 bar, preferably at normal pressure. The distillative isolation of the products can be carried out at a pressure from 0.01 bar to 1 bar, preferably at normal pressure.

The mole ratio of the triorganoboroxin 1 to the alkylborate 2 can vary in a wide range. However, it is preferred that the mole ratio is in the range of approximately 1:2 to 1:4, preferably in the range of approximately 1:3.

Furthermore, when $R^1$ is methyl the trimethylboroxin (1a) can be prepared in a pre step in situ followed by the reaction of (1a) with a trialkylborate (2) of the formula $B(OR^2)_3$, preferably in the same reactor. In this case diborane gas is reacted with carbon monoxide to yield the desired (1a) of the formula $(H_3C—BO)_3$ in THF solution (Scheme 1, Brown, H. C. Organometallics 4, 816 (1984), Rathke, M. W.; Brown, H. C. J. Am. Chem. Soc. 88, 2606 (1966)).

Scheme 1

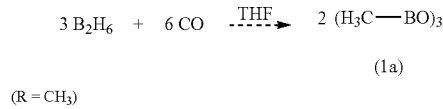

(R = $CH_3$)

Another embodiment of the invention is therefore a process for the preparation of a dialkoxymethylborane (3a) of the formula $H_3C—B(OR^2)_2$, comprising the steps of
a) reacting diborane with carbon monoxide in a solvent to form the trimethylboroxin 1a of the formula $(H_3C—BO)_3$,
b) reacting the trimethylboroxin (1a) with a trialkylborate (2) of the formula $B(OR^2)_3$, and c) separating the dialkoxymethylborane from the reaction mixture by distillation,
wherein $R^2$ is $C_1$-$C_{20}$ alkyl
or two $R^2$ groups in compound (2) together with the —$BO_2$— moiety form a cyclic structure of the formula

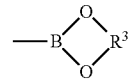

with the divalent group $R^3$ selected from the group consisting of —$CH_2CH_2$—, —$CH(CH_3)CH_2$—, —$CH_2CH_2CH_2$—, —$CH(CH_3)CH(CH_3)$—, —$CH(CH_2CH_3)CH_2$—, —$C(CH_3)_2$ $C(CH_3)_2$—, —$CH_2C(CH_3)_2CH_2$—, —$(CH_2)_6$—, ortho-$C_6H_4$ or ortho-$C_6H_3$alkyl.

According to another embodiment of the invention the synthesis of trialkoxyboroxins (4) of the formula $(R^2O—BO)_3$ involves an ester exchange reaction between a triorganoboroxin (1) of the formula $(R^1—BO)_3$ and a trialkylborate (2) of the formula $B(OR^2)_3$,
wherein
$R^1$ is $C_1$-$C_{20}$ alkyl, $C_3$-$C_{10}$ cycloalkyl, $C_6$-$C_{14}$ aryl, $C_7$-$C_{24}$ aralkyl, $C_7$-$C_{24}$ alkaryl, $C_2$-$C_{20}$ alkenyl, $C_5$-$C_{15}$ cycloalkenyl, $C_2$-$C_{20}$ alkynyl, $CH_2SiMe_3$, substituted $C_1$-$C_{20}$ alkyl
and
$R^2$ is $C_1$-$C_{20}$ alkyl.

According to the invention the dialkoxyorganoboranes (3) can be employed for the synthesis of organo-oxazaborolidine catalysts (organo-CBS).

Another object of the present invention is therefore a process for the preparation of organo-oxazaborolidines of the structural formula (6)

(6)

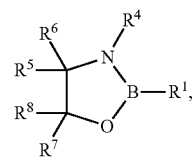

comprising the steps of
a) reacting an 1,2-aminoalcohol of the formula (5)

$HNR^4$—$CR^5R^6CR^7R^8$—OH    (5)

wherein
$R^4$ to $R^8$ is hydrogen, $C_1$-$C_{20}$ alkyl, $C_6$-$C_{14}$ aryl, $C_7$-$C_{24}$ aralkyl, $C_7$-$C_{24}$ alkaryl, substituted $C_1$-$C_{20}$ alkyl
or the two groups $R^4$ and $R^5$ together are a divalent group selected from the group consisting of —$CH_2CH_2$—, —$CH(CH_3)CH_2$—, —$CH_2CH_2CH_2$—, —$CH(CH_3)CH(CH_3)$—, —$CH(CH_2CH_3)CH_2$—, —$C(CH_3)_2C(CH_3)_2$—, —$CH_2C(CH_3)_2CH_2$— to form with the —NH—$CR^6$— moiety a cyclic structure,
with a dialkoxyorganoborane 3 of the formula $R^1$—B $(OR^2)_2$, wherein
$R^1$ is $C_1$-$C_{20}$ alkyl, $C_3$-$C_{10}$ cycloalkyl, $C_6$-$C_{14}$ aryl, $C_7$-$C_{24}$ aralkyl, $C_7$-$C_{24}$ alkaryl, $C_2$-$C_{20}$ alkenyl, $C_5$-$C_{15}$ cycloalkenyl, $C_2$-$C_{20}$ alkynyl, $CH_2SiMe_3$, substituted $C_1$-$C_{20}$ alkyl
and
$R^2$ is $C_1$-$C_{20}$ alkyl
or the two $R^2$ groups in compound (3) together with the —$BO_2$— moiety form a cyclic structure of the formula

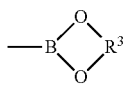

with the divalent group R³ selected from the group consisting of —CH₂CH₂—, —CH(CH₃)CH₂—, —CH₂CH₂CH₂—, —CH(CH₃)CH(CH₃)—, —CH(CH₂CH₃)CH₂—, —C(CH₃)2C(CH₃)₂—, —CH₂C(CH₃)₂CH₂—, —(CH₂)₆—, ortho-C₆H₄ or ortho-C₆H₃alkyl, and b) heating the reaction mixture to complete the ring closure reaction and to distill off the formed alcohol.

Preferably chiral 1,2-aminoalcohols (5) are employed in this process. Chiral 1,2-aminoalcohols are characterized by the presence of at least one asymmetric carbon atom. Preferably 1,2-aminoalcohols (5) with different R⁵ and R⁶ groups and/or different R⁷ and R⁸ groups are employed.

Scheme 2 shows an example using diisopropoxymethylborane (3b) to prepare (S)-MeCBS (6a) from (S)-diphenylprolinol (5a) (c.f. U.S. Pat. No. 4,943,635). Instead of water isopropanol is produced as a side product, which can easily be removed from the catalyst.

Scheme 2

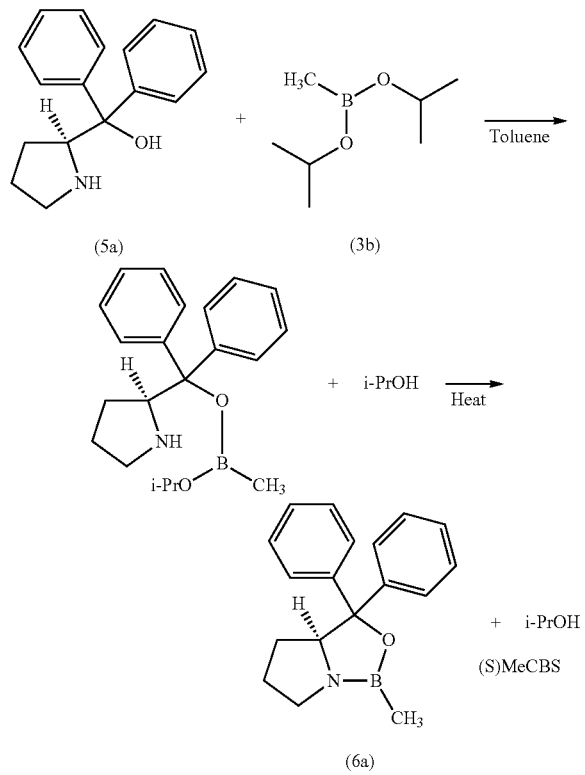

The reaction mixture is heated in step b) of the process described above to a temperature sufficient to complete the ring closure reaction in short time, preferably in less than 3 hours. This is usually achieved by heating the reaction mixture to the reflux temperature of the solvent or solvent mixture employed under normal pressure. Regular temperature ranges for this step are between about ambient temperatures and about +120° C.

The process is usually performed at a pressure from 0.1 bar to 5 bar, preferably at normal pressure. The distillative separation of the formed alcohol can usually be carried out at a pressure from 0.01 bar to 1 bar, preferably at normal pressure.

Another potential use of dialkoxyorganoboranes is in Suzuki-type C—C-bond coupling reactions to transfer an organo group into a molecule.

As used in connection with the present invention, the term "alkyl" denotes a branched or an unbranched or a cyclic saturated hydrocarbon group comprising between 1 and 20 carbon atoms; examples are methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and isopinocampheyl. Preferred are the alkyl groups methyl, ethyl, propyl, isopropyl, butyl, isobutyl, sec-butyl, tert-butyl, amyl, isoamyl, sec-amyl, 1,2-dimethylpropyl, 1,1-dimethylpropyl.

The term "cycloalkyl" denotes a saturated hydrocarbon group comprising between 3 and 10 carbon atoms including a mono- or polycyclic structural moiety. Examples are cyclopropyl, cyclobutyl, cyclopentyl, cyclohexyl, cycloheptyl, cyclooctyl, cyclononyl or cyclodecyl. Preferred are the cycloalkyl groups cyclopropyl, cyclopentyl and cyclohexyl.

The term "substituted alkyl" denotes an alkyl group with at least one hydrogen atom is replaced by a halide atom like fluorine, chlorine, bromine or iodine or by an alkoxy group.

The term "alkoxy" stands for a group derived from an aliphatic monoalcohol with between 1 and 20 carbon atoms.

The term "alkenyl" denotes a straight chain or branched unsaturated hydrocarbon group comprising between 2 and 20 carbon atoms including at least one carbon-carbon double bond. Examples are vinyl, allyl, 1-methylvinyl, butenyl, isobutenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1,4-pentadienyl, 1,3-hexadienyl, 1,4-hexadienyl. Preferred are the alkenyl groups vinyl, allyl, butenyl, isobutenyl and 1,3-butadienyl.

The term "cycloalkenyl" denotes an unsaturated hydrocarbon group comprising between 5 and 15 carbon atoms including at least one carbon-carbon double bond and a mono- or polycyclic structural moiety. Examples are cyclopentenyl, 1-methylcyclopentenyl, cyclohexenyl, cyclooctenyl, 1,3-cyclopentadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

The term "alkynyl" denotes a straight chain or branched unsaturated hydrocarbon group comprising between 2 and 20 carbon atoms including at least one carbon-carbon triple bond. Examples of alkynyl groups include ethynyl, 2-propynyl and 2- or 3-butynyl.

The term "aryl" denotes an unsaturated hydrocarbon group comprising between 6 and 14 carbon atoms including at least one aromatic ring system like phenyl or naphthyl or any other aromatic ring system. ortho-$C_6H_4$ denotes a divalent aryl group occurring in catechol-type derivatives.

The term "aralkyl" denotes an aryl-substituted alkyl group comprising between 7 and 24 carbon atoms including for example a phenyl-, naphthyl- or alkyl-substituted phenyl- or alkyl-substituted naphthyl-group or any other aromatic ring system. Examples of aralkyl groups include benzyl, 1- or 2-phenylethyl, 1-, 2- or 3-phenylpropyl, mesityl and 2-, 3- or 4-methylbenzyl groups.

The term "alkaryl" denotes an alkyl-substituted aryl group comprising between 7 and 24 carbon atoms including for example a phenyl- or naphthyl- or alkyl-substituted phenyl- or alkyl-substituted naphthyl-group or any other aromatic ring system and an alkyl substituent as defined above. Examples for alkaryl groups are 2-, 3- or 4-methylphenyl, 2-, 3- or 4-ethylphenyl and 2-, 3-, 4-, 5-, 6-, 7- or 8-methyl-1-naphthyl groups. ortho-$C_6H_3$alkyl denotes an alkyl-substituted divalent aryl group occurring in catechol-type derivatives.

EXAMPLES

The following examples illustrate the present invention without limitation of the same.

Example 1

Synthesis of Diisopropoxymethylborane

Triisopropylborate (110 g, 0.585 mol) was added to trimethylboroxin (55 ml of a 50 wt % solution of trimethylboroxin in THF, 0.20 mol) under nitrogen and stirred for 5 minutes. The resulting clear solution was heated to distill off the desired diisopropoxymethylborane through a Vigreux column. The first fraction (22 g, distilling between 66-71° C.) contained mostly THF and a small amount of isopropanol. The second fraction (53 g, distilling between 74-100° C.) contained 81 wt % diisopropoxymethylborane and 19 wt % THF. The third fraction (24 g, distilling between 100-112° C.) contained 87 wt % diisopropoxymethylborane and 13 wt % triisopropoxyboroxin. The overall yield of diisopropoxymethylborane was 75.8% relative to the borate employed.

Example 2

Synthesis of Diisopropoxymethylborane with Preceding Formation of trimethylboroxin Trimethylboroxin was prepared in a pressure reactor by addition of diborane (86 g, 3 moles) and carbon monoxide (excess) into THF (150 ml) containing lithium borohydride catalyst (0.25 g). The reaction temperature was kept below 50° C. during the gas addition. Some of the diborane was swept from the reactor by the excess CO vented, therefore the final amount of solution obtained was 197 g. The resulting concentration of trimethylboroxin in THF was 39.3 wt % by boron analysis. This solution containing 77 g trimethylboroxin was combined with triisopropylborate (348.8 g, 1.85 mol). The mixture was fractionally distilled. The first fraction (100 ml, 70-88° C.) contained THF, diisopropoxymethylborane and pyrophoric trimethylborane as an impurity and was discarded. Fraction 2 (90 ml, distilled between 88-98° C.) and fraction 3 (150 ml, distilled between 98-120° C.) both contained primarily diisopropoxymethylborane (impurities <5%), giving an estimated yield of about 70%.

Example 3

Synthesis of Methyldi-n-butoxyborane

Trimethylboroxin (50 ml of 50 wt % solution in THF, 170 mmol) was placed in a round bottom flask with distillation head and receiver under nitrogen. Tri-n-butyl borate (92 ml, 340 mmol) was added and the mixture stirred 30 min. Methyldi-n-butoxyborane and THF were distilled from the tri-n-butoxyboroxin. The methyldi-n-butoxyborane and THF were separated by further distillation to obtain 44 g of methyldi-n-butoxyborane, 50% yield.

Example 4

Synthesis of (S)-MeCBS from Methyldi-n-butoxyborane (S)-Diphenylprolinol (DPP) (0.58 g, 2.3 mmol) along with 15 ml of toluene were added to a 50 ml three-neck round bottom flask fitted with a distillation head and condenser and flushed with nitrogen. While remaining under inert atmosphere, methyldi-n-butoxyborane (0.60 g, 2.3 mmol) was added via syringe to the flask. The reaction contents were heated to 110° C. while stirring for 1 hour. While the $^{11}B$ NMR spectrum of the reaction mixture showed the formation of intermediates δ=9.7 ppm), additional methyldi-n-butoxyborane (0.06 g, 0.23 mmol) was added followed by heating for 4 hours. All toluene and 1-butanol were distilled from the clear reaction mixture (azeotrope boiling point 106° C.). Toluene was added to the residue. The $^{11}B$ NMR spectrum of the toluene solution showed complete formation of (S)-MeCBS (δ=35 ppm, broad singlet). The $^1H$ NMR spectrum ($CDCl_3$) of the product also indicated no remaining (S)-DPP or unreacted methyldi-n-butoxyborane.

The invention claimed is:
1. A process for the preparation of organo-oxazaborolidines of the structural formula (6)

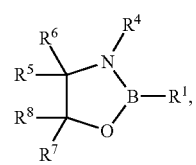

(6)

comprising the steps of
a) reacting an 1,2-aminoalcohol of the formula (5)

$HNR^4—CR^5R^6CR^7R^8—OH$ (5)

wherein
$R^4$ to $R^8$ is hydrogen, $C_1$-$C_{20}$ alkyl, $C_6$-$C_{14}$ aryl, $C_7$-$C_{24}$ aralkyl, $C_7$-$C_{24}$ alkaryl, substituted $C_1$-$C_{20}$ alkyl
or the two groups $R^4$ and $R^5$ together are a divalent group selected from the group consisting of —$CH_2CH_2$—, —$CH(CH_3)CH_2$—, —$CH_2CH_2CH_2$—, —$CH(CH_3)CH(CH_3)$—, —$CH(CH_2CH_3)CH_2$—, —$C(CH_3)_2C(CH_3)_2$—, —$CH_2C(CH_3)2CH2$— to form with the —NH—$CR^6$— moiety a cyclic structure,
with a dialkoxyorganoborane (3) of the formula $R^1$—B$(OR^2)_2$, wherein $R^1$ is $C_1$-$C_{20}$ alkyl, $C_3$-$C_{10}$ cycloalkyl, $C_6$-$C_{14}$ aryl, $C_7$-$C_{24}$ aralkyl, $C_7$-$C_{24}$ alkaryl, $C_2$-$C_{20}$ alkenyl, $C_5$-$C_{15}$ cycloalkenyl, $C_2$-$C_{20}$ alkynyl, $CH_2SiMe_3$, substituted $C_1$-$C_{20}$ alkyl and $R^2$ is $C_1$-$C_{20}$ alkyl or the two $R^2$ groups in compound (3) together with the $BO_2$— moiety form a cyclic structure of the formula

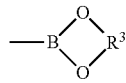

with the divalent group $R^3$ selected from the group consisting of —$CH_2CH_2$—, —$CH(CH_3)CH_2$—, —$CH_2CH_2CH_2$—, —$CH(CH_3)CH(CH_3)$—, —$CH(CH_2CH_3)CH_2$—, —$C(CH_3)_2C(CH_3)_2$—, —$CH_2C(CH_3)_2CH_2$—, —$(CH_2)_6$—, ortho-$C_6H_4$ or ortho-$C_6H_3$alkyl, and b) heating the reaction mixture to complete the ring closure reaction and to distill off the formed alcohol.

2. The process according to claim 1 wherein the 1,2-aminoalcohol (5) is chiral.

* * * * *